(12) United States Patent
Hurt et al.

(10) Patent No.: US 9,261,513 B1
(45) Date of Patent: Feb. 16, 2016

(54) ANTIBODY BIOMARKER SPECIFIC FOR MITOTIC CELLS AND RELATED METHODS

(71) Applicant: Florida State University Research Foundation, Inc., Tallahassee, FL (US)

(72) Inventors: Myra Hurt, Tallahassee, FL (US); Raed Rizkallah, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 11 days.

(21) Appl. No.: 14/330,209

(22) Filed: Jul. 14, 2014

Related U.S. Application Data

(62) Division of application No. 13/235,882, filed on Sep. 19, 2011, now Pat. No. 8,829,160.

(60) Provisional application No. 61/383,921, filed on Sep. 17, 2010.

(51) Int. Cl.
*C07K 16/18* (2006.01)
*G01N 33/68* (2006.01)

(52) U.S. Cl.
CPC ............ *G01N 33/6872* (2013.01); *C07K 16/18* (2013.01)

(58) Field of Classification Search
CPC .............................. G01N 33/6872; C07K 16/18
See application file for complete search history.

(56) References Cited

U.S. PATENT DOCUMENTS 4,444,879 A * 4/1984 Foster et al. ................. 435/7.95

OTHER PUBLICATIONS

Rizkallah et al. Regulation of the Transcription Factor YY1 in Mitosis through Phosphorylation of Its DNA-binding Domain, Molecular Biology of the Cell, 20: 4766-4776 (Nov. 15, 2009).*
Dovat et al. A common mechanism for mitotic inactivation of C2H2 zinc finger DNA-binding domains, Genes & Dev. 16: 2985-2990 (2002).*
Jantz et al., Reduction in DNA-binding affinity of Cys2 HIS2 zinc finger proteins by linker phosphorylation, Department of Biophysics and Biophysical Chemistry, John Hopkins University School of Medicine, Baltimore, MD 21205, www.pnas.org/cgi/doi/10.1073/pnas.0402191101, May 18, 2004.
Rizkallah et al., Regulation of the Transcription Factor YY1 in Mitosis through Phosphorylation of its DNA-binding Domain, Molecular Biology of the Cell, vol. 20, 4766-4776, Nov. 15, 2009.
Dovat et al., A common mechanism for mitotic inactivation of C2H2 zinc finger DNA-binding domains, Genes & Dev. 2002, 16-:2985-2990.
Kim et al. Prognostic significance of the mitotic index using the mitosis marker anti-phosphohistone H3 in meningiomas, Am J Clin Patol 128: 118-125 (2007).

* cited by examiner

*Primary Examiner* — Gail R Gabel
(74) *Attorney, Agent, or Firm* — Christopher M. Ramsey; GrayRobinson, P.A.

(57) ABSTRACT

An isolated antibody having a specific binding affinity for a polypeptide comprising the amino acid sequence HTEGKP (SEQ ID NO: 2) phosphorylated at threonine is described. The antibody may be used as biomarker for mitotic cells. A method for using the antibody includes contacting a cell with the antibody and detecting antibody bound to the cell as an indicator of the cell being in the mitotic state. A reagent kit comprising the antibody is also described.

12 Claims, 12 Drawing Sheets
(8 of 12 Drawing Sheet(s) Filed in Color)

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Thr Gly Glu Lys Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

His Thr Gly Glu Lys Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Thr Gly Asp Arg Pro
1               5
```

ANTIBODY BIOMARKER SPECIFIC FOR MITOTIC CELLS AND RELATED METHODS

CROSS REFERENCE TO RELATED APPLICATIONS

This is a division of application Ser. No. 13/235,882, filed Sep. 19, 2011, now U.S. Pat. No. 8,829,160, which claims priority to provisional application Ser. No. 61/383,921, filed Sep. 17, 2010. The entire contents of these prior applications are incorporated by reference herein.

FIELD OF THE INVENTION

This invention relates to the field of biomarkers and, more particularly, to biomarkers specific for mitotic cells.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated by reference herein in its entirety.

BACKGROUND

Mitosis is the biological process in which new cells are formed from existing cells. During mitosis, the chromosomes in a cell's nucleus are separated into two identical sets. After the identical sets of chromosomes are formed, the cell undergoes a process called cytokinesis in which the cell's nucleus, cytoplasm, organelles and cell membrane divide to form two daughter cells.

The cell cycle is a series of stages that a cell passes through in leading up to replicating itself. Together, mitosis and cytokinesis define the mitotic phase. The mitotic phase may be further broken down into several different stages, namely, prophase, metaphase, anaphase, telophase, and cytokinesis. During prophase, the duplicated chromosomes condense and become visible under a microscope. During metaphase the chromosomes align in the center of the cell before being separated into two cells. During anaphase, the duplicated chromosomes separate into two sets. During telophase, nuclei form around the separated chromosomes. In order to complete mitosis an intricate network of signaling pathways that orchestrates the mitotic physical and biochemical processes converge. Accurate coordination of all these pathways is vital for the execution of mitosis and proper distribution of the genetic material into the two new daughter cells.

Phosphorylation, a process in which a phosphate group is added to a protein or other organic molecule, acts as an on/off switch for many biological functions and is responsible for inactivating many transcription factors. Research has shown that certain zinc finger peptides (ZFPs) are phosphorylated at their linker peptides, causing them to lose DNA binding activity in mitotic cells. The present inventors realized that phosphorylation of the ZFP linker peptides could be a common pathway for inactivation of all $C_2H_2$ ZFPs during mitosis. Accordingly, the present inventors have developed a way to target these linker peptides by using an antibody that binds to the phosphorylated forms of the linker peptides.

SUMMARY

In view of the foregoing, it is an object of the invention is to provide an isolated antibody that has a specific binding affinity to a polypeptide comprising SEQ ID NO: 2 phosphorylated at threonine. The isolated antibody may be polyclonal or monoclonal. The antibody may advantageously used as a biomarker for mitotic cells, to identify stages of the cell cycle, or as a prognostic aid in cellular proliferation.

In an embodiment of the invention, the antibody may be used to identify a eukaryotic cell in the mitotic state according to a method comprising contacting the cell with an antibody having specific binding affinity for SEQ ID NO: 2 phosphorylated at threonine and detecting antibody bound to the cell as an indicator of the cell being in the mitotic state.

According to another embodiment of the invention, a method for detecting mitotic cells within a eukaryotic cell population is provided. In this embodiment, the method comprises contacting the cell population with an antibody specific for SEQ ID NO: 2 phosphorylated at threonine and detecting cells within the population having bound antibody as indicative of being in the mitotic state. This or other methods of the invention may be advantageously adapted to determine a mitotic index, wherein the mitotic index is expressed as a ratio of the number of cells having bound antibody with the number of cells having no bound antibody.

According to another embodiment of the invention, a method of immunostaining cells is provided. The method comprises contacting the cells with an antibody having specific affinity for a cellular marker indicative of the mitotic state, said marker comprising SEQ ID NO: 2 when phosphorylated at threonine. The method may further comprise staining the cells with a secondary antibody comprising a fluorescent marker.

In embodiments of the invention detection of cells or an antibody may be accomplished by using a preferred process selected from western blotting, flow cytometry, immunostaining, and microscopy or a combination thereof.

In the methods of use, the cells are preferably eukaryotic cells, and more preferably mammalian cells. However, any cell comprising SEQ ID NO: 2 phosphorylated at threonine may be targeted by the antibody.

According to another embodiment of the invention, a reagent kit comprising an antibody having a specific binding affinity for an amino acid sequence comprising SEQ ID NO: 2 phosphorylated at threonine is provided. The kit may be used for testing one or more samples of cells using western blotting, flow cytometry, immunostaining, and microscopy or a combination thereof for the detection of mitotic cells. The kit may further comprise suitable additional reagents that are used in these techniques.

These and other objects, aspects, and advantages of the present invention will be better appreciated in view of the drawings and following detailed description of the preferred embodiments.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENTS

Figure 1:
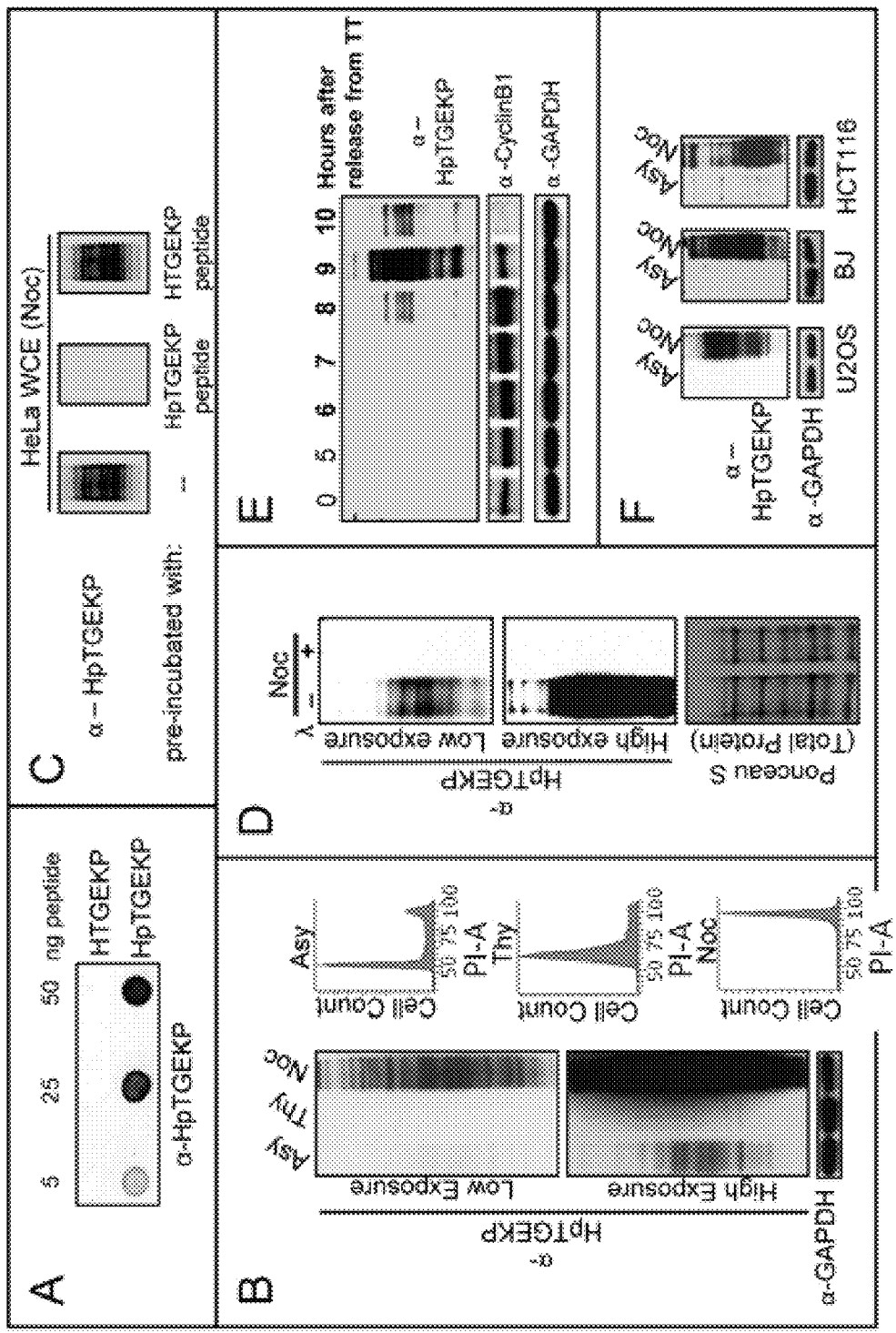
FIG. 1A-F shows mitotic specificity of the HpTGEKP phosphorylation. (A) Dot-blot assay of non-phosphorylated (HTGEKP (SEQ ID NO: 2)) and phosphorylated (HpT-GEKP) synthetic peptides probed with α-HpTGEKP. (B) Western blot of WCEs from HeLa cells, growing asynchronously (Asy), arrested with thymidine (Thy), or with nocodazole (Noc). The blot was probed with α-HpTGEKP, then stripped and reprobed with α-GAPDH as a loading control. Fractions of the collected cells were fixed, stained with propidium iodide and analyzed using FACS to show cell cycle distribution based on DNA content (PI-A). (C) Western blot of WCEs from nocodazole-arrested HeLa cells probed with α-HpTGEKP pre-incubated with HTGEKP (SEQ ID NO: 2) or HpTGEKP synthetic peptides, as indicated. (D) Western blot of WCEs from nocodazole-arrested HeLa cells incubated with or without Lambda phosphatase. The blot was probed with α-HpTGEKP, and then stained with Ponceau S to show equal loading and the total distribution of protein bands in both lanes. (E) Western blot of WCEs from HeLa cells synchronized at early S-phase by double-thymidine block, and released for the indicated time points. The blot was probed with α-HpTGEKP, then stripped and reprobed with α-GAPDH as a loading control, and α-cyclin B1 to monitor cell cycle progression. (F) Western blots of WCEs from U2OS, BJ, and HCT116 asynchronously (Asy) growing or arrested with nocodazole (Noc). The blot was probed with α-HpTGEKP, and then stripped with α-GAPDH as a loading control.

In the Summary of the Invention above and in the Detailed Description of the Preferred Embodiments, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will be thorough and complete, and will convey the scope of the invention to those skilled in the art.

As used herein, the following terms have the following meanings:

"antibody" means a peptide or protein produced by an organism in response to the presence of a specific foreign antigen and includes fragments thereof comprising the antigen binding region;

"contacting" means placement in direct physical association and includes both solid and liquid form;

"HpTGEKP" means the polypeptide HTGEKP (SEQ ID NO: 2) phosphorylated at threonine;

"α-HpTGEKP" means the antibody that specifically binds to HpTGEKP;

"mitotic index" means a measure for the proliferation status of a cell population defined by the ratio between the number of cells in mitosis and the total number of cells;

"reagent kit" means a collection of materials, including one or more reagents, related to performing a test or procedure; and "specific binding affinity" means the ability of an individual antibody combining site to react with a specific antigenic determinant or the ability of a population of antibody molecules to react with a specific antigen.

A hallmark of cell division is the cessation of active transcription [1,2]. Although compaction of DNA into condensed chromosomes results in a restrictive barrier, it is not solely responsible for the inhibition of transcription [3,4]. Entry into mitosis is accompanied by waves of phosphorylation events regulating the large morphological changes like DNA condensation and nuclear envelope disassembly [5]. Phosphorylation has also been shown to be a key player in turning off transcriptional activity, both through general and specific mechanisms [3]. The general mechanisms usually involve the inactivation of various components of the basic transcriptional machinery, like phosphorylation of RNA Polymerase II and TFIIH [6-8]. In addition, various context-specific phosphorylation events have been shown to differentially inactivate sequence-specific transcription factors, like Myc and Myb [9]. The simultaneous inactivation of a whole class of sequence specific transcription factors by a common mechanism has never been shown although two such mechanisms have been proposed. The first is for the POU homeodomain containing transcription factors, such as Oct-1 and GHF-1 [10, 11] and the second is for the $C_2H_2$ zinc finger proteins [12].

$C_2H_2$ ZFPs represent the largest class of DNA binding transcription factors comprising hundreds of members in the human genome [13]. $C_2H_2$ ZFPs are involved in a very wide spectrum of functional diversity, regulating biological processes like cellular growth, proliferation, and differentiation [14,15]. Each ZFP usually comprises several zinc finger modules which dictate its sequence-specific DNA binding activity. However, optimal binding activity of a ZFP is achieved through cooperative binding of adjacent zinc fingers wrapping around the DNA in locking position [14,16]. Small five amino acid linker peptides join adjacent zinc fingers and are critical for this locking position regardless of the sequence specificity of the bound DNA. These linkers are highly conserved among the different ZFPs with TGEKP (SEQ ID NO: 1) being the consensus, and most prevalent, sequence [14, 16-18].

The DNA binding efficiency and specificity of the clusters of zinc finger domains has led to a significant amount of research aimed at designing artificial ZFPs. These have been used to perform a variety of engineered functions at specific targets in the genome, such as controlled gene expression and nuclease activity [19-22]. The naturally occurring, and very common, sequence TGEKP (SEQ ID NO: 1) has also been used as the linker peptide in most of these designed ZFPs [20]. Although several of the amino acid residues in linker peptides can affect the efficient binding to DNA, [17,23,24] the conserved threonine (or serine) residue has a particularly important role, especially through its hydroxyl group [25]. This same hydroxyl group can be modified by phosphorylation, resulting in significant reduction of binding affinity [26].

Two $C_2H_2$ ZFPs, Ikaros and Sp1, have been shown to be phosphorylated at their linker peptides, causing them to lose DNA binding activity in mitotic cells [12]. In a study of the ZFP YY1, it was shown that loss of DNA binding activity and exclusion from chromatin during mitosis were also due to phosphorylation of its linker peptides [27].

As discussed in the examples below, the inventors have developed an antibody that has a specific binding affinity to a phosphorylated form of TGEKP (SEQ ID NO: 1). The particular phosphorylated sequence comprises HpTGEKP. Due to the prevalence of HpTGEKP in mitotic cells, the antibody (α-HpTGEKP) may be used for many advantageous purposes, including those disclosed here. Using α-HpTGEKP the inventors have successfully detected massive and simultaneous mitotic phosphorylation of hundreds of zinc finger proteins. This wave of phosphorylation is tightly synchronized, starting in mid-prophase after DNA condensation and before the breakdown of the nuclear envelope. This global phosphorylation is reversed in telophase. In addition, the exclusion of the phospho-linker signal from condensed DNA clearly demonstrates a common mechanism for the mitotic inactivation of $C_2H_2$ ZFPs.

In the following sections, experimental evidence of the phosphorylation of $C_2H_2$ ZFP linker peptide by α-HpTGEKP in mitosis is provided. The data and discussion provided are by way of example only and, therefore, do not limit the scope of the invention in any way.

EXAMPLES

Abundance of $C_2H_2$ Linker Phosphorylation in Mitotic Cells

The $C_2H_2$ ZFP family comprises hundreds of members each containing several linker peptides, in some cases even dozens [13,14]. If a common mechanism for the inactivation of $C_2H_2$ ZFPs through phosphorylation of their linker peptides does exist, these conserved phosphosites should be found in high abundance. To investigate this, we searched high-throughput databases from published large-scale mass spectrometry analyses [28-32]. Indeed, hundreds of phospho-linker peptides have been mapped. However, these reported phosphosites were not particularly categorized under ZFPs or associated with any specific functional relevance. To illustrate the results of this search, we chose fifty ZFPs containing the consensus linker sequence TGEKP (SEQ ID NO: 1). Table 1 lists fifty examples of zinc finger proteins, their sizes (in amino acid residues), NCBI accession number, and location(s) of TGEKP (SEQ ID NO: 1) amino acid sequence(s). Only TGEKP linker peptides were considered in this search and displayed in this table. All TGEKP (SEQ ID NO: 1) linker peptides of each of the listed proteins have been indicated with their amino acid location(s) within each protein. TGEKP (SEQ ID NO: 1) linker peptides that have been reported to be phosphorylated are indicated with the corresponding reference(s) of their report(s).

To enable the experimental investigation of this global mitotic event, we developed an antibody against the phosphorylated form of the consensus linker sequence (pTGEKP). To increase the immunogenicity and specificity of the epitope, we included a histidine residue N-terminally to this sequence. The histidine is part of the preceding zinc finger and is conserved in all $C_2H_2$ ZFPs, forming the phospho-epitope HpTGEKP.

First, to test the phospho-specificity of the α-HpTGEKP antibody, we spotted synthetic non-phosphorylated or phosphorylated HTGEKP (SEQ ID NO: 2) peptides onto a nitrocellulose membrane. As shown in FIG. 1A, α-HpTGEKP efficiently recognized only the phosphorylated form of the linker peptide.

Next, we prepared whole cell extracts (WCE) from HeLa cells growing asynchronously, arrested with thymidine (S-phase), or with nocodazole (pro-metaphase of mitosis). Proteins were separated on SDS-PAGE gel, transferred to a nitrocellulose membrane. When the blot was probed with α-HpTGEKP antibody, a large number of bands were detected only in the lane containing proteins extracted from nocodazole-arrested cells. This shows that the phospho-epitope HpTGEKP is found on many proteins in mitotic cells. High exposure of the blot revealed fainter bands in the asynchronous lane but not the thymidine lane. This is reasonable since an asynchronous population typically contains a small percentage of mitotic cells. Equal loading of proteins in the three lanes was controlled for by probing with the GAPDH antibody, and synchrony of the cells confirmed by propidium iodide staining and flow cytometry analyses (FIG. 1B).

To test the specificity of the detected bands, WCEs from nocodazole-arrested HeLa cells were probed with α-HpTGEKP pre-incubated with or without the synthetic peptides HTGEKP (SEQ ID NO: 2) or HpTGEKP. As shown in FIG. 1C, pre-incubation of the antibody with the non-phosphorylated linker peptide (HTGEKP (SEQ ID NO: 2)) did not affect the signal. However, pre-incubation with HpTGEKP completely abolished the signal. Furthermore, pre-treatment of the protein extracts from nocodazole-arrested cells with phosphatase caused the complete disappearance of all bands, even at high exposure, showing the high phospho-specificity of the α-HpTGEKP antibody (FIG. 1D).

Figure 2:
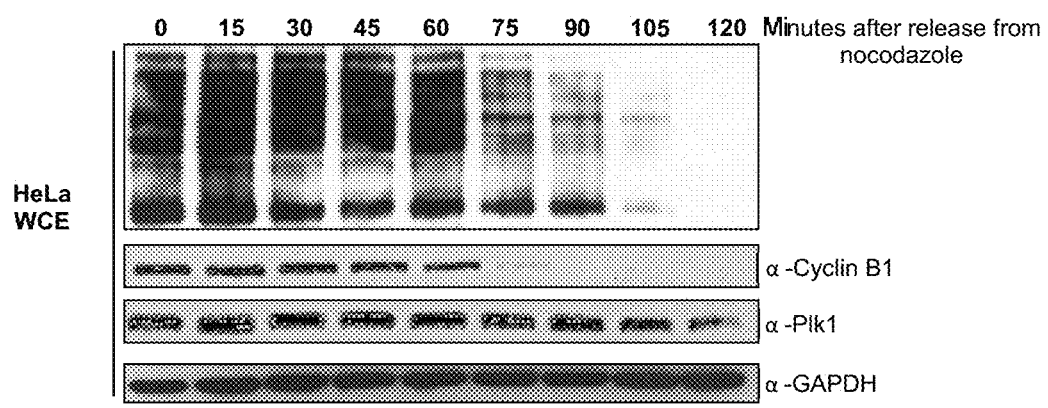
FIG. 2 is Western blot data of WCEs from HeLa cells synchronized at pro-metaphase with nocodazole and released for the indicated time points. The blot was probed with α-HpTGEKP, then stripped and reprobed with α-GAPDH as a loading control, and α-cyclin B1 and α-Plk1 to monitor progression through mitosis.

Next, we wanted to ensure that the observed bands are not an artifact of the nocodazole arrest and to determine the timing of this phosphorylation in the cell cycle. For this, HeLa cells were synchronized by double-thymidine block, released, and cells were collected for WCE preparation at 5, 6, 7, 8, 9, and 10 hours after release (FIG. 1E). The progression from S-phase, through G2, and through mitosis was monitored by cyclin B1 levels. [33] Probing with α-HpTGEKP antibody generated bands peaking at 9 hours, when the majority of the cells are in mitosis. The bands rapidly disappeared as cell started exiting mitosis at the 10-hour time point (FIG. 1E). In addition, probing WCE from HeLa cells that were released from a nocodazole block, showed that the HpTGEKP bands disappeared as cells progressed towards the end of mitosis (FIG. 2).

To exclude the possibility that this massive mitotic phosphorylation event is specific to HeLa cells, WCEs from asynchronous or nocodazole arrested U2OS, BJ, and HCT116 cells were probed with the α-HpTGEKP antibody. The results were similar to those obtained using HeLa cells (FIG. 1F).

Specificity of α-HpTGEKP to Individual $C_2H_2$ ZFPs

Next, we wanted to test the specificity of the new antibody to mitotic phosphorylation of individual ZFPs. The high number of bands detected in WCEs makes it particularly difficult to evaluate individual proteins based on their size distribution. Therefore, conclusive results cannot be obtained by stripping and reprobing the blot with individual ZFP antibodies. Instead, our approach was to immunoprecipitate individual ZFPs using protein-specific antibodies from the WCE and probe for HpTGEKP phosphorylation.

YY1 is a multifunctional $C_2H_2$ ZFP involved in the regulation of a wide array of genes controlling cellular growth, proliferation, differentiation, apoptosis, [34,35] and tumorigenesis [36, 37]. YY1 contains four zinc fingers, all of which are needed for its optimal DNA binding activity [38,39]. We have previously shown that YY1 gets phosphorylated at two of its linker peptides during mitosis, linker 2 (TGEKP (SEQ ID NO: 1)) and linker 3 (TGDRP (SEQ ID NO: 3). We have also shown that mitotic phosphorylation of YY1 at these linkers results in loss of DNA binding activity and exclusion from the condensed DNA [27].

To test if α-HpTGEKP could detect mitotic YY1, Flag-YY1 was immunoprecipitated from HeLa-Flag-YY1 stable transfectant cells, either growing asynchronously or nocodazole-arrested. The resulting Western blot with α-YY1 antibody showed equal Flag-YY1 protein levels in the immunoprecipitates from asynchronous or nocodazole protein extracts. However, α-HpTGEKP antibody only detected Flag-YY1 in the α-Flag IP from nocodazole extracts (FIG. 3A). In addition, we show that this signal is phospho-specific, since phosphatase treatment of the immunoprecipitated Flag-YY1 from nocodazole extracts abolished the signal (FIG. 3B). YY1 contains only one HTGEKP (SEQ ID NO: 2) sequence (threonine 348 of YY1). To examine the specificity of the antibody to its target sequence within YY1, Flag-YY1 wild type (WT) or a threonine to alanine mutant (T348A) were transiently overexpressed in HeLa cells. Each transfection was then divided into two, one growing asynchronously and the other was blocked with nocodazole. Flag-YY1 (WT) and (T348A) were then immunoprecipitated and probed with α-YY1 antibody, showing equal Flag-YY1 protein levels in all of the IPs. While α-HpTGEKP recognized mitotic Flag-YY1 (WT), it did not detect Flag-YY1 (T348A) (FIG. 3C). Since both TGEKP (SEQ ID NO: 1) and TGDRP (SEQ ID NO: 3) are phosphorylated on mitotic YY1,[27] this result clearly demonstrates the specificity of α-HpTGEKP for its target phospho-epitope.

CTCF is another multifunctional ZFP involved in gene regulation and multiple levels of chromatin organization [40, 41]. The CTCF protein contains several linker peptides, but only one contains the exact TGEKP (SEQ ID NO: 1) sequence (threonine 518). Probing immunoprecipitated CTCF from asynchronous or nocodazole arrested HeLa cells with α-HpTGEKP shows that it is phosphorylated at this site in mitosis (FIG. 3D). To our knowledge, this particular CTCF site has not been previously reported to be phosphorylated.

Dynamic Distribution of $C_2H_2$ Linker Phosphorylation During Mitosis

Figure 4:
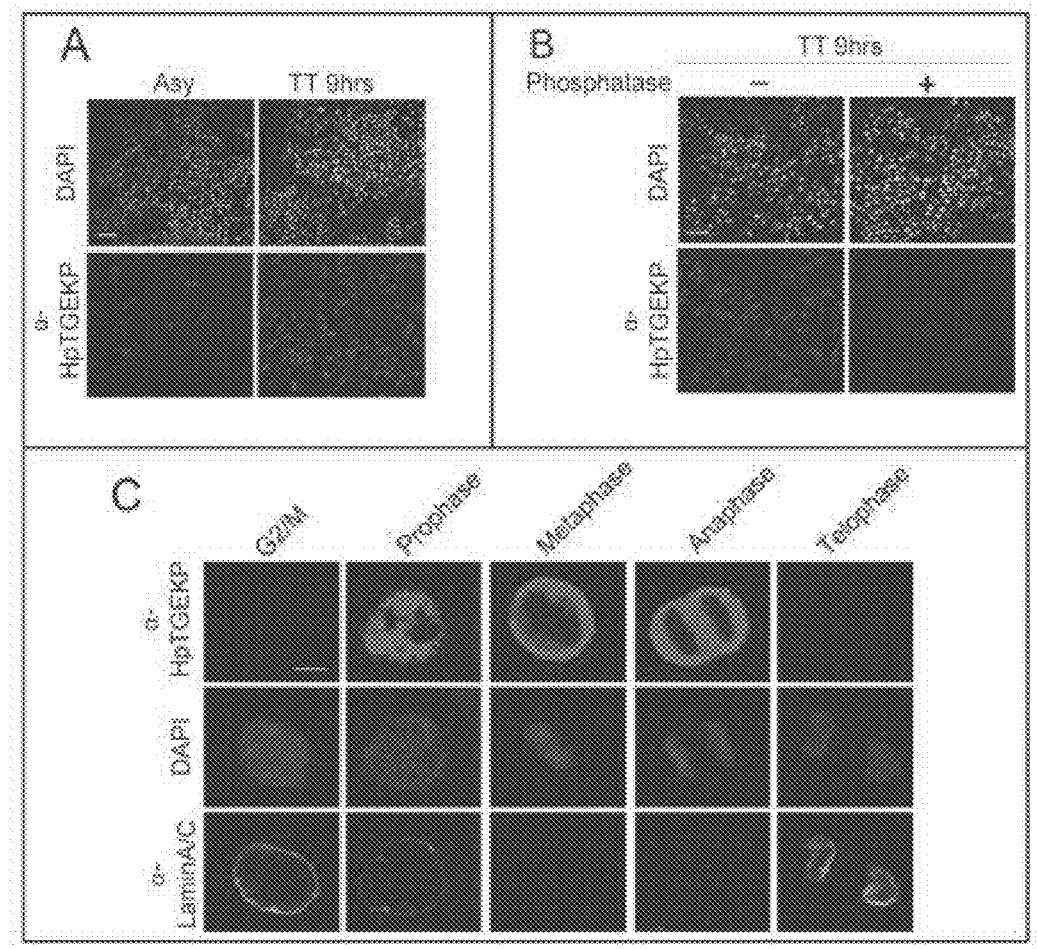
FIG. 4A-C shows the timing and distribution of linker phosphorylation during mitosis. HeLa cells were grown on coverslips, fixed, permeabilized, and stained. Images were captured on a fluorescent confocal microscope. Specific mitotic stage labeling was based on chromatin morphology. (A) HeLa cells, asynchronously growing (Asy) or synchronized with double-thymidine block and released for 9 hours (TT9 hrs). Cells were stained with DAPI (blue) and α-HpTGEKP (red). (scale bar=100 μM). (B) HeLa cells (TT9 hrs) treated with or without Lambda phosphatase prior to immunostaining. Cells were stained with DAPI (blue) and α-HpTGEKP (red). (scale bar=100 μM). (C) HeLa cells synchronized with double-thymidine block and collected 8-10 hours after release. Cells were stained with DAPI (blue), α-HpTGEKP (red), and α-lamin A/C (green, to visualize the nuclear envelope). (scale bar=20 μM).

The results presented in the two previous figures, showing western blot analysis, demonstrate the high abundance of linker phosphorylation in mitotic cells. However, the best approach to delineate the exact timing of linker peptide phosphorylation during mitosis is to observe its occurrence in individual cells. Therefore, to study the temporal and spatial distribution of linker peptide phosphorylation during mitosis we immunostained HeLa cells with α-HpTGEKP and examined them using confocal microscopy. Cell nuclei (DNA) were visualized with DAPI stain. First, we looked at cells at low magnification. FIG. 4A shows that few cells were positive for HpTGEKP phosphorylation in an asynchronous HeLa population. However, all of the positive cells had condensed chromatin (not shown), suggesting the exclusivity of the phosphorylation to mitotic cells. These positive cells were highly enriched when cells were synchronized with double-thymidine block and released for 9 hrs (TT9 hrs). This conforms to the Western blot results in FIG. 1E. The immunostaining was confirmed to be phospho-specific, since treatment of HeLa (TT9 hrs) cells with Lambda phosphatase abolished the signal (FIG. 4B).

Figure 5:
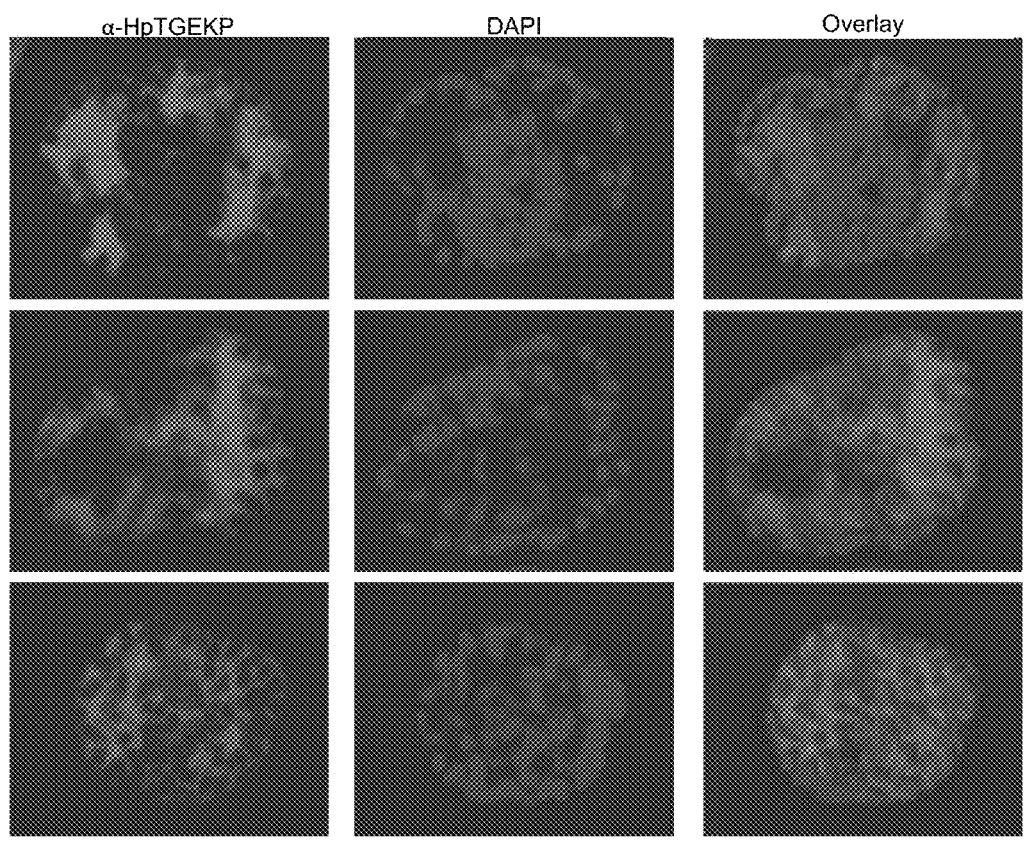
FIG. 5 shows the exclusion of HpTGEKP signal from condensed DNA in prophase. HeLa cells were grown on coverslips, synchronized with double thymidine and released for 8 hours. Cells were fixed and immunostained with α-HpTGEKP (red) and DAPI (blue). Images of three HeLa cells in prophase were captured on a fluorescent confocal microscope.
Figure 6:
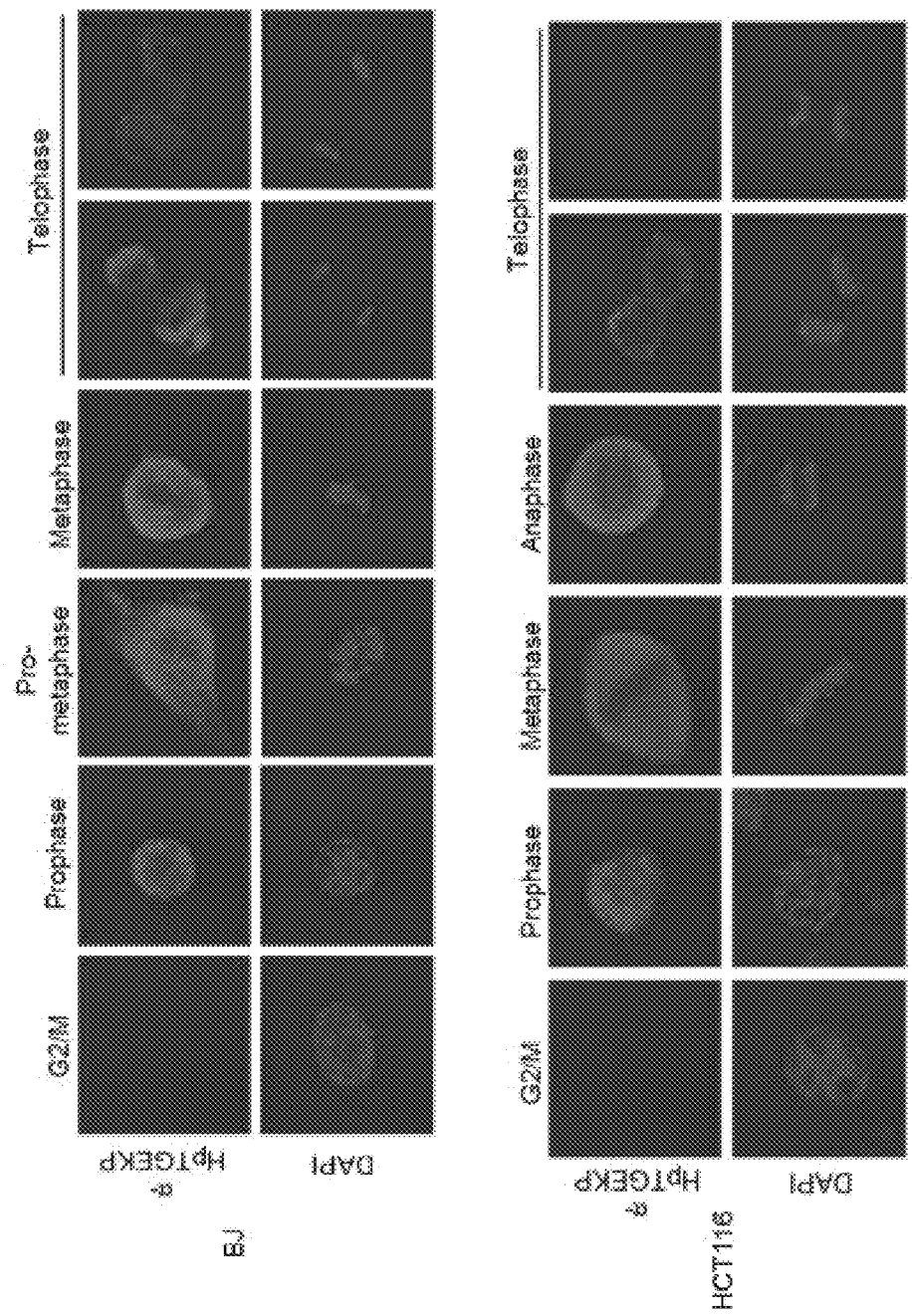
FIG. 6 shows HpTGEKP timing and distribution in BJ and HCT116 cell lines. BJ and HCT116 were grown on coverslips, synchronized with thymidine and released for 8-11 hours. Cells were then fixed, permeabilized, and immunostained with α-HpTGEKP (red) and DAPI (blue). Images were captured on a fluorescent confocal microscope. Specific mitotic stage labeling was based on chromatin morphology.

To investigate the sub-mitotic dynamics of HpTGEKP phosphorylation, we examined individual mitotic HeLa cells at high magnification. Cells were double-immunostained with α-HpTGEKP and with α-Lamin A/C to visualize the nuclear envelope. DNA was stained with DAPI and the chromatin morphology was used to determine the mitotic stages. FIG. 4C shows that HpTGEKP phosphorylation occurs in prophase prior to the nuclear envelope disassembly. HpTGEKP phosphorylation persists through metaphase, anaphase, and is dephosphorylated by the end of telophase. Throughout these stages, the HpTGEKP signal is excluded from the condensed DNA, as is clearly shown in the metaphase and anaphase panels of FIG. 4C and in the prophase panel in FIG. 5. These observations support the hypothesis that mitotic phosphorylation of linker peptides abolishes the DNA binding activity of ZFPs and contributes to their dispersal away from condensed chromosomes during mitosis. Similar immunostaining patterns were observed for BJ and HCT116 cells (FIG. 6).

Figure 7:
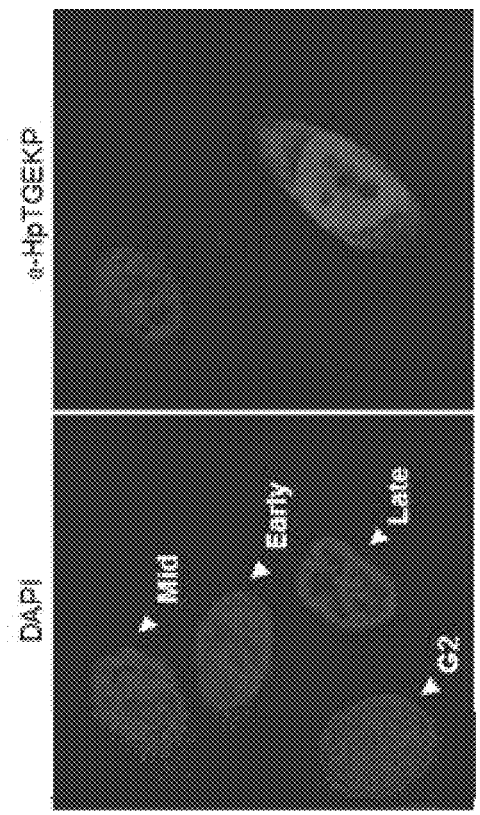
FIG. 7 shows timing of HpTGEKP phosphorylation and cellular distribution during prophase. HeLa cells were grown on coverslips synchronized by double-thymidine block and released for 8.5 hours, fixed, permeabilized, and stained with DAPI (blue) and α-HpTGEKP (red). Images were captured on a fluorescent confocal microscope. Images show cells in late G2, early, mid, and late prophase based on their chromatin morphology.
Figure 7:
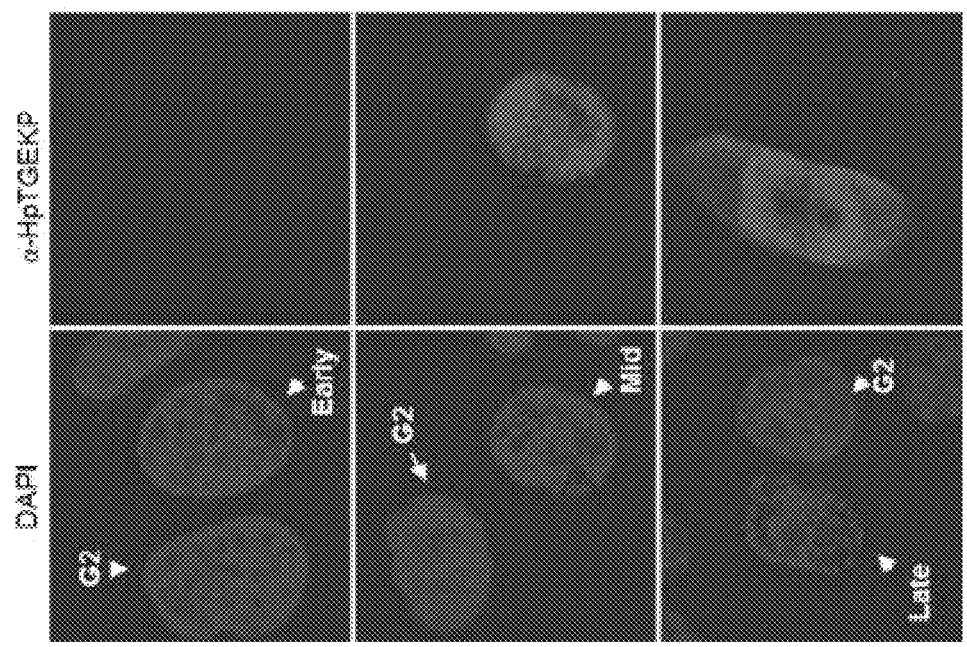
Figure 8:
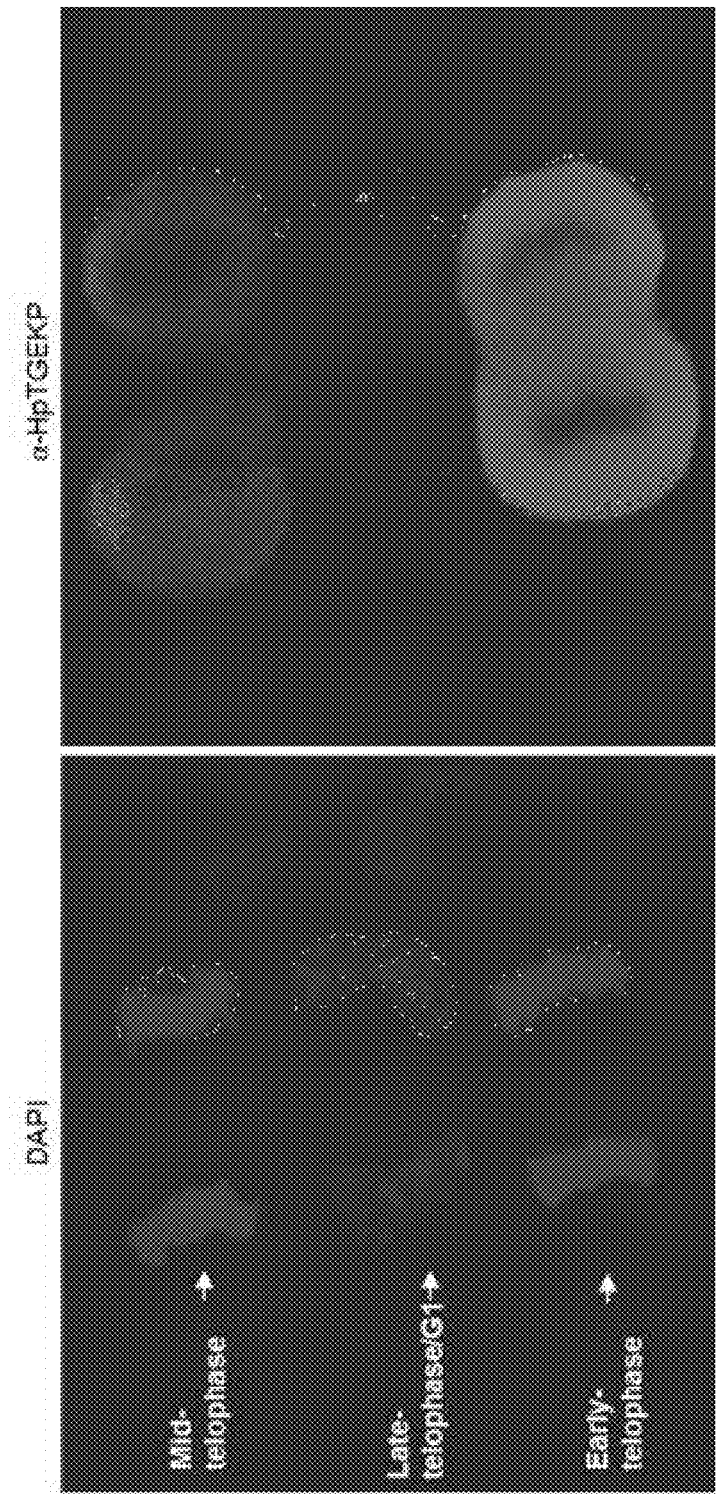
FIG. 8 shows HpTGEKP dephosphorylation during telophase. HeLa cells were grown on coverslips synchronized by double-thymidine block and released for 9.5 hours, fixed, permeabilized, and stained with DAPI (blue) and α-HpTGEKP (red). The image was captured with a fluorescent confocal microscope and shows three cells at the end of mitosis, at three different stages of telophase, based on their chromatin morphology, and the extent of the cleavage furrow of cytokinesis.

To further dissect the initial timing of the HpTGEKP phosphorylation, we investigated HeLa cells at several stages of prophase by monitoring the chromosome condensation morphologies. We found that HpTGEKP phosphorylation occurs in mid-prophase (FIG. 7). Interestingly, the signal is initially nuclear and distributes to the cytoplasm only at late-prophase, a stage that is associated with the breakdown of the nuclear envelope. Therefore, the presence of this phosphorylation does not appear to be sufficient to translocate the modified ZFPs to the cytoplasm. We have previously shown that phospho-mimetic mutations in the linker peptides of the ZFP YY1 inactivate its DNA binding activity but do not affect its nuclear localization [27]. We have also shown that YY1 distribution to the cytoplasm occurs at late prophase.[27] This indicates that linker phosphorylation excludes ZFPs from the condensing DNA, but their cytoplasmic distribution is probably due to a different mechanism associated with the disruption of the nuclear envelope barrier. On the other hand, dephosphorylation of HpTGEKP occurs gradually during telophase and cytokinesis, and is complete at the end of mitosis (FIG. 8).

Figure 9:
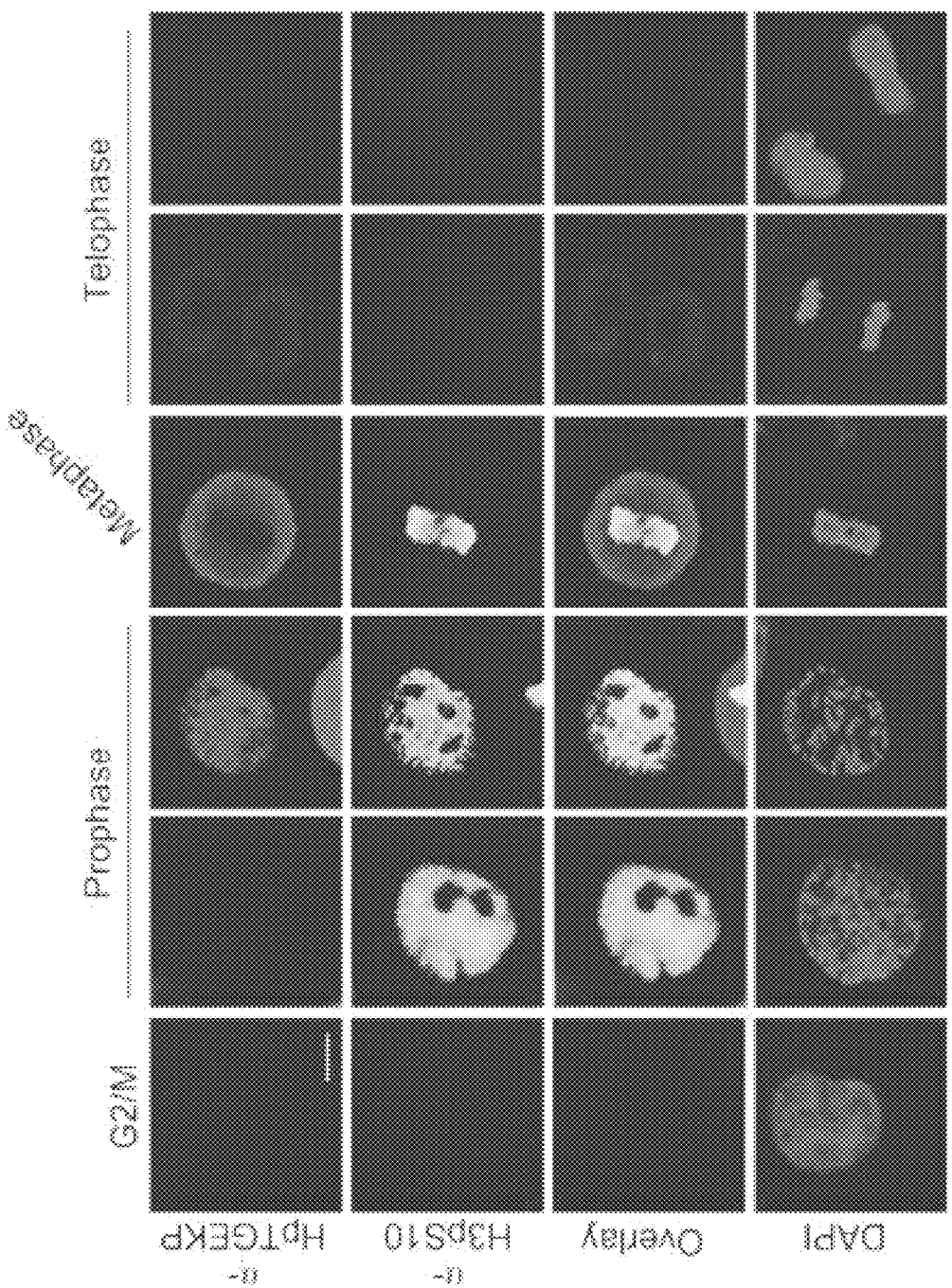
FIG. 9 shows Temporal correlation between phosphorylation of HpTGEKP and pH3S10. HeLa cells grown on coverslips were synchronized by double-thymidine block, released, and collected 8-10 hours after release. Cells were stained with DAPI (blue) and immunostained with α-HpTGEKP (red) and α-pH3S10 (green). Specific mitotic stage labeling was based on chromatin morphology. (Bar, 20 μM).
Figure 10:
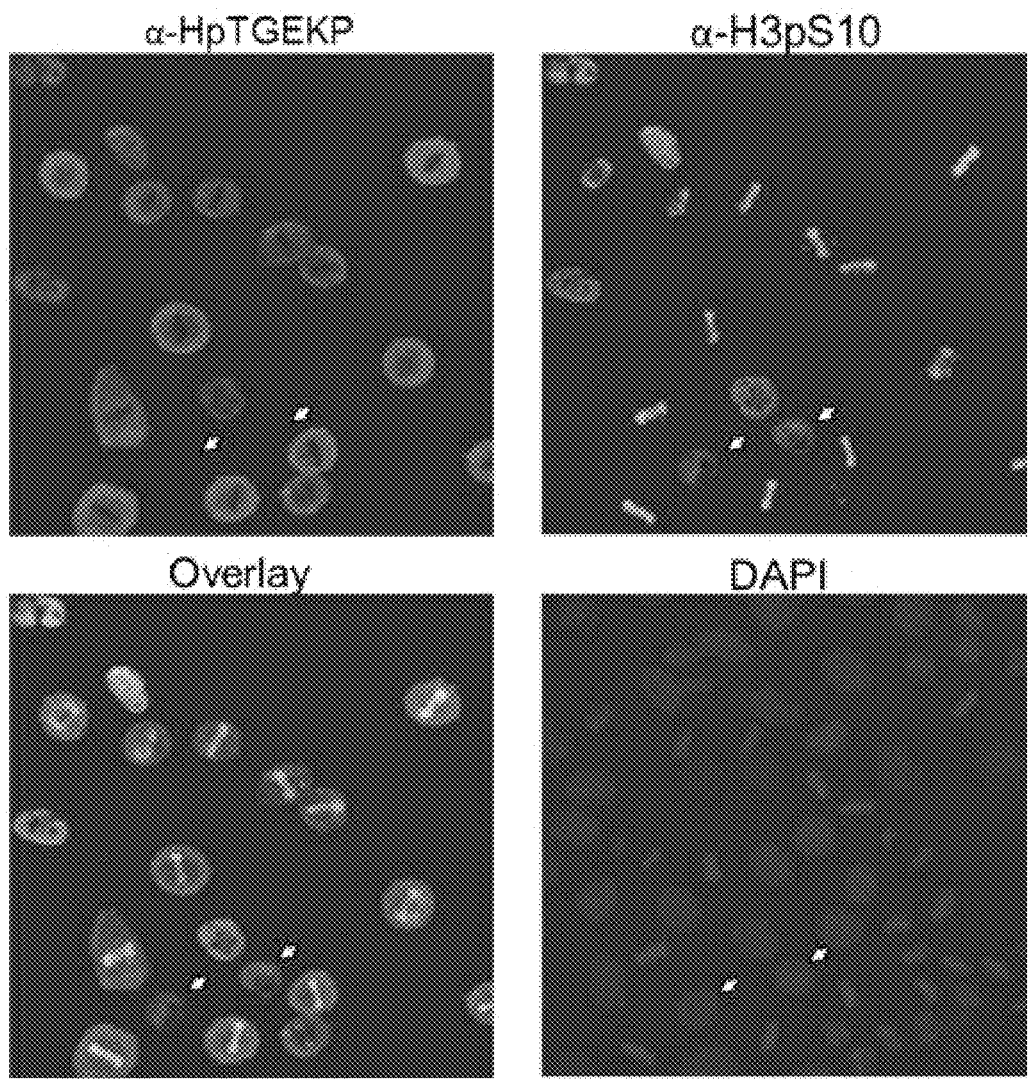
FIG. 10 shows that pH3S10 phosphorylation briefly precedes that of HpTGEKP. This confocal image shows a mixed population of HeLa cells at different stages of G2, prophase and metaphase. HeLa cells were grown on coverslips synchronized with a single thymidine block and released for ~9 hours, fixed, permeabilized, and stained with DAPI (blue), α-HpTGEKP (red), and pH3S10 (green). This image shows that most mitotic cells display both α-HpTGEKP and pH3S10 phosphorylation. However, two cells have pH3S10 phosphorylation prior to HpTGEKP phosphorylation, as indicated by arrows.

Histone H3 serine 10 phosphorylation (pH3S10) is a widely used mitotic marker. This phosphorylation can occur in specific contexts in association with gene expression. However, its prominent and global distribution is specific to mitosis and is correlated with DNA condensation [42-44]. To further characterize the timing of α-HpTGEKP phosphorylation, double-immunostaining of mitotic HeLa cells was performed using α-HpTGEKP and α-pH3S10 antibodies. FIG. 9 and FIG. 10 show a large overlap in the timing of both phosphorylation events. However, HpTGEKP appears slightly later than pH3S10 and persists longer in telophase. In addition, overlay images show a clear exclusion of the two signals.

The HpTGEKP Phospho-Epitope is an Efficient Mitotic Marker

Figure 3:
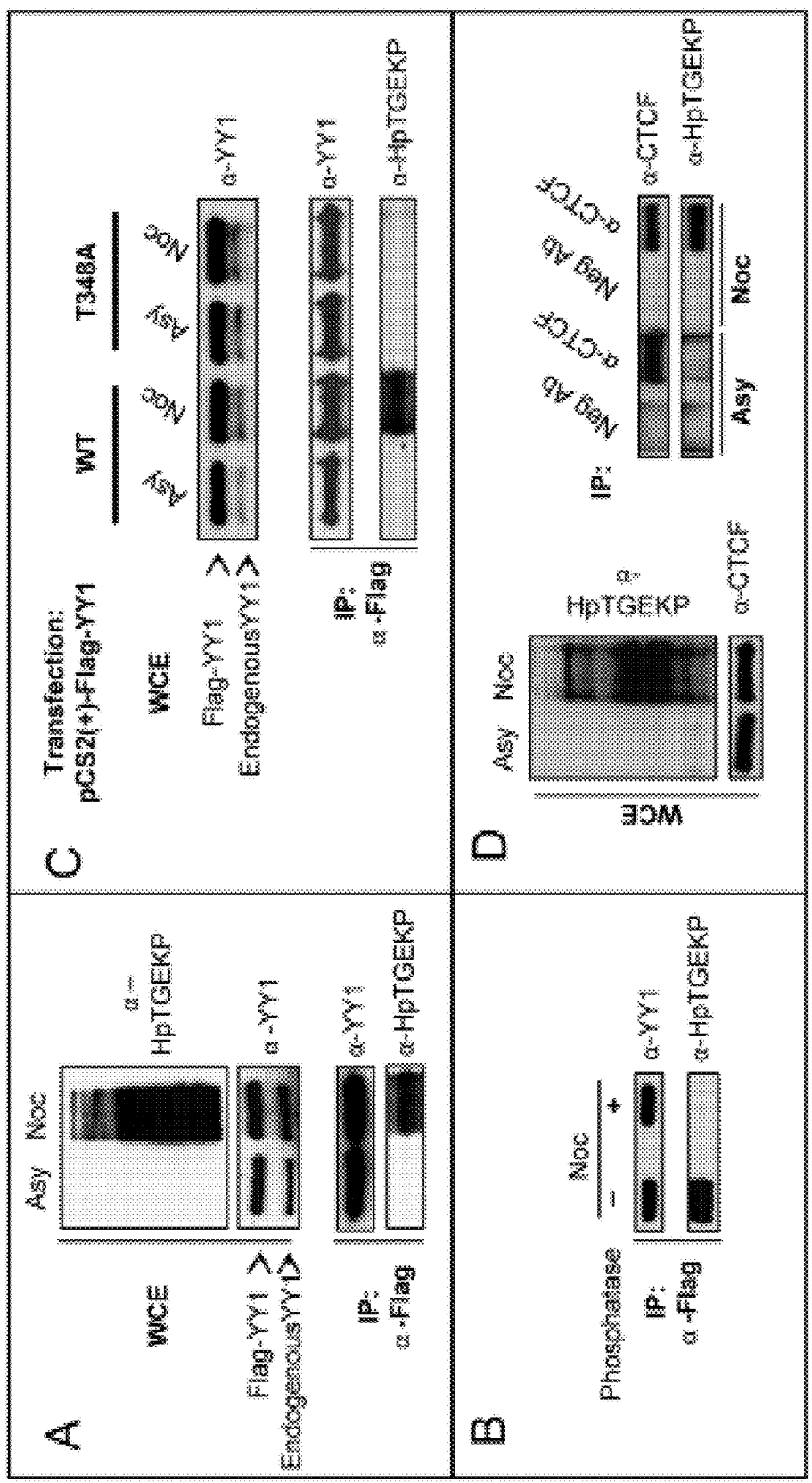
FIG. 3A-D shows the detection HpTGEKP phosphorylation on specific ZFPs. (A) Western blot of WCEs of HeLa-Flag-YY1 cells growing asynchronously (Asy) or arrested with nocodazole (Noc), probed with α-HpTGEKP, and then α-YY1 (upper panel). Western blot of α-Flag IP from HeLa-Flag-YY1 extracts (Asy or Noc), probed with α-YY1, then with α-HpTGEKP (lower panel). (B) Western blot of α-Flag IP from HeLa-Flag-YY1 extracts (Noc) pre-treated with or without Lambda phosphatase. The blot was probed with α-YY1, then with α-HpTGEKP. (C) Western blot of WCEs of HeLa cells transiently overexpressing Flag-YY1 (WT) or (T348A) (Asy or Noc). The blot was probed with α-YY1 (upper panel). Western blot of α-Flag IP, probed with α-YY1, then with α-HpTGEKP (lower panel). (D) Western blot of WCEs of HeLa cells (Asy or Noc), probed with α-HpTGEKP, and then stripped and reprobed with α-CTCF (left panel). Western blot of α-CTCF IP, probed with α-CTCF, then with α-HpTGEKP (right panel). Anti-GFP was used as the negative control antibody.

Whether in the context of understanding natural human growth and development or related pathologies, like cancer, the study of the cell cycle and proliferation is largely dependent on efficient and precise biomarkers. Our results clearly demonstrate that the α-HpTGEKP antibody has great potential as a useful proliferation and mitotic marker. Due to the high abundance of the HpTGEKP phospho-epitope in mitotic cells, it is easily detectable in Western blot analyses (FIGS. 1 and 3). In immunostaining and low magnification fluorescent microscopy, the signal generated from probing with α-HpTGEKP epitope is an indication of the proliferative state of the cellular population (FIG. 4A). At high magnification, linker phosphorylation marks mid-prophase, immediately subsequent to the condensation of DNA (FIG. 4C and FIG. 7). The spatial distribution of HpTGEKP phosphorylation offers a clearly visible indicator of progression through prophase. The breakdown of the nuclear envelope is a major morphological event of late prophase [5]. The exact timing of the breakdown of the nuclear envelope barrier is difficult to assess based on the visible morphological changes of the envelope itself. As mentioned earlier, the linker phosphorylation excludes the ZFPs from mitotic chromatin but is not sufficient for cytoplasmic export; which happens at later mitotic stages in the absence of the nuclear envelope [27]. Therefore, the spatial distribution of HpTGEKP signal from the nuclear to the cytoplasmic space in late prophase can be used to mark the exact breaking point of the nuclear envelope barrier (FIG. 7).

Figure 11:
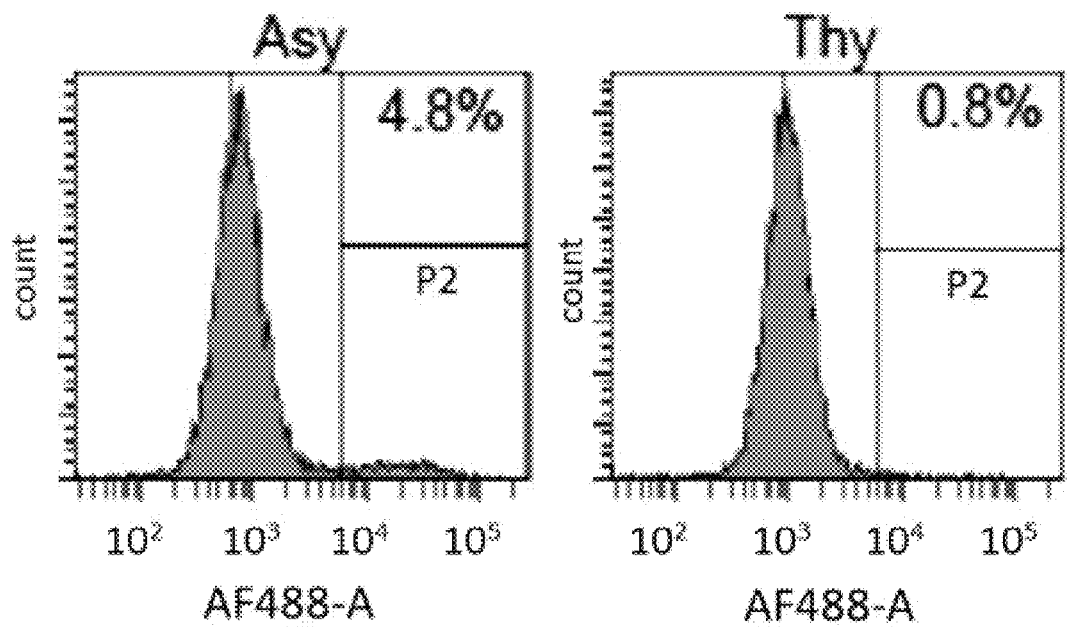
FIG. 11 is a mitotic index calculation for asynchronous (Asy) and thymidine-arrested (Thy) HeLa cells using α-HpTGEKP staining.
Figure 12:
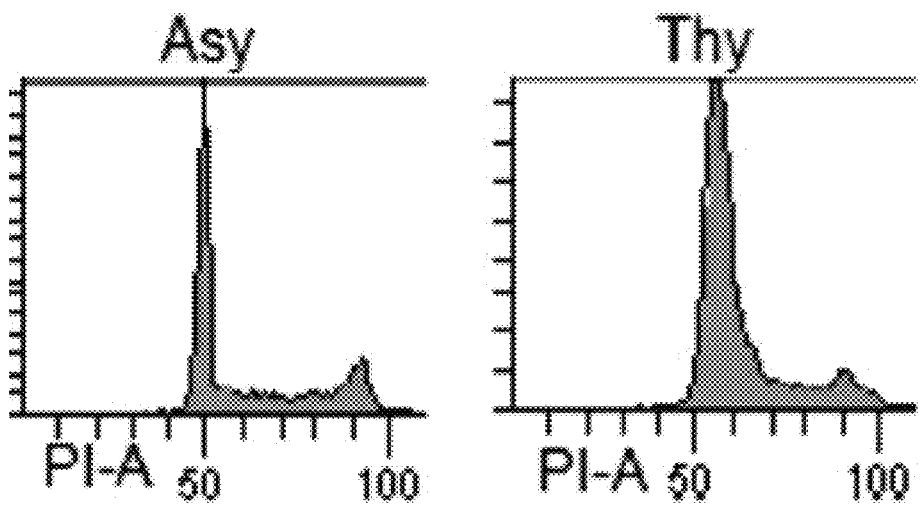
FIG. 12 is a control experiment from the samples of FIG. 11 using propidium iodide staining for cell cycle analysis based on DNA content.

The efficiency of the HpTGEKP immunostaining makes it a good candidate for the quantitative calculation of the mitotic index and enrichment of mitotic cells using flow cytometry analyses. To assess this, asynchronously growing or thymidine-arrested HeLa cells were trypsinized and fixed, and then each population was aliquoted into two fractions. One fraction was immunostained with α-HpTGEKP and the other stained with propidium iodide as a control for cell cycle distribution. As shown in FIG. 11, the signal generated from fluorescent immunostaining was very strong (about 100 fold higher than the auto and background fluorescence), allowing gating and calculation of positive cells. According to this result, 4.8% of the asynchronously growing HeLa cells were mitotic compared to only 0.8% in the thymidine arrested cells. This indicates that the thymidine block was not entirely complete and some mitotic cells are present in the population. Conforming to this result, the propidium iodide staining also showed a small peak of 4N DNA content (FIG. 12). pH3S10 immunostaining is the most commonly used marker to calculate mitotic index. To compare mitotic index calculations from these two markers, asynchronous HeLa cells were immunostained with α-HpTGEKP or α-pH3S10, and a third fraction of the cells was stained with propidium iodide to control for normal asynchronous cell cycle distribution (not shown). When calculated using either antibody, the mitotic index was very similar (Results from a triplicate sample: 4.7%±0.36 for HpTGEKP and 4.63%±0.32 for pH3S10).

Figure 13:
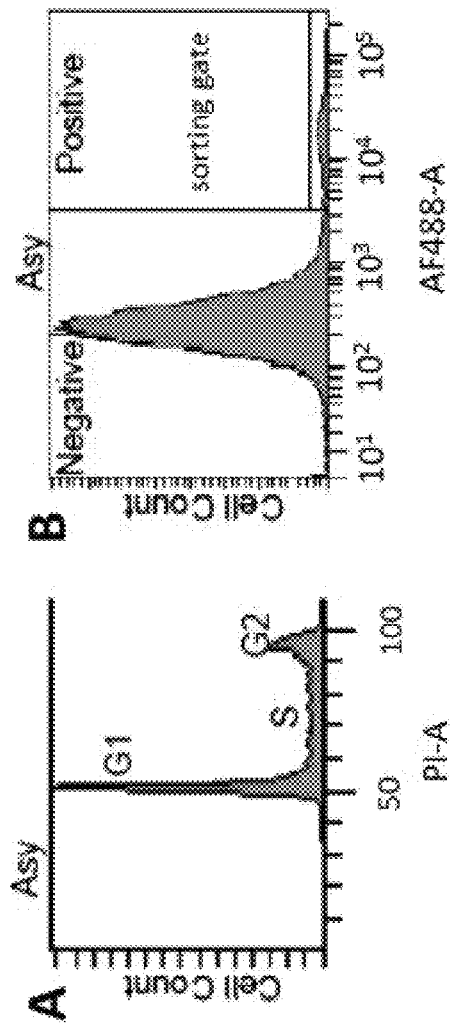
FIG. 13A-B shows data in which synchronous HeLa cells were trypsinized and collected. (A) A fraction of the cells was stained with propidium iodide for cell cycle analysis based on DNA content. (B) Another fraction was immunostained with α-HpTGEKP and a secondary antibody was coupled to Alexa Fluor 488 fluorescent dye. There was about 100-fold difference in the AF488 intensities between background and positive HpTGEKP staining, allowing gating and sorting of cells.
Figure 14:
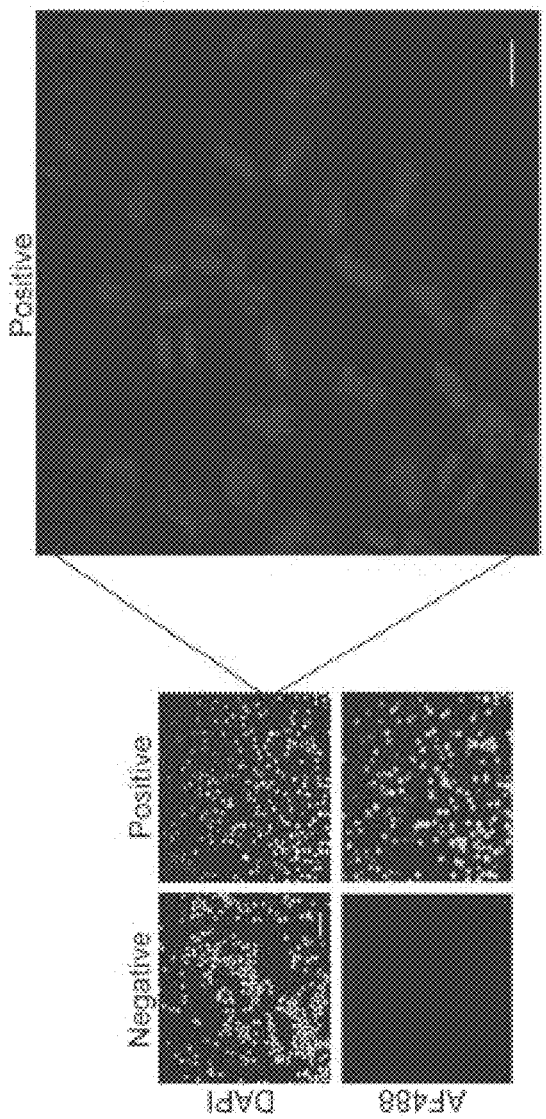
FIG. 14 shows data in which the samples in FIG. 13 B from the sorted (negative and positive) fractions were stained with DAPI and observed using a fluorescent microscope (scale bar=100 μM) (lower left images). The right panel shows higher magnification examination of the DNA content of the positive cells showing various mitotic phases (scale bar=20 μM).

In addition, we explored the potential capacity of the new marker for enrichment and purification of mitotic cells. For this purpose, an asynchronous population of HeLa cells was immunostained with α-HpTGEKP. Negatively and positively stained cells were sorted using flow cell cytometry. Samples from each fraction were stained with DAPI and examined under a fluorescent microscope. FIG. 13 shows the sorting efficiency; all the positively sorted cells displayed AF488 (HpTGEKP) staining, but none of the negatively sorted cells. When examined at higher magnification, all of the positively sorted cells displayed mitotic condensed chromosomes, indicating high sorting efficiency of mitotic cells (FIG. 14). Also, all the mitotic stages were represented in the positive fraction. To allow flexibility in subsequent biochemical analyses alternative fixation methods (like, ethanol fixation) were tested, and yielded comparable results in all assays (data not shown).

Discussion

The study of the simultaneous modification of hundreds of proteins is challenging. To enable the characterization of this biological phenomenon, we exploited the high conservation of the linker peptides, which is the basis of the common phosphorylation pathway. ZFP linker peptides display high sequence similarities with some degree of divergence that would be tolerated as a phosphorylation consensus site, but not for immunogenic specificity. Interestingly, more than half of these ZFP linkers are composed of the same five-amino acid sequence (TGEKP (SEQ ID NO: 1) [14]. In addition, the linker of $C_2H_2$ ZFPs is preceded by the second histidine residue of the preceding zinc finger.

The specificity of α-HpTGEKP to its phosphorylated target sequence was proven using different approaches, with synthetic peptides or individual ZFPs (YY1 and CTCF), as shown above. We used this antibody in Western blots to show the massive and global nature of this phosphorylation event on a large number of proteins. Using immunostaining techniques and fluorescent microscopy, we showed the tight synchrony of this massive event and its mitotic exclusivity. Taken together, these temporal and spatial observations fit perfectly with the proposed biological function of this modification, which is the inactivation of DNA binding activity of $C_2H_2$ ZFPs and their exclusion from condensed chromatin during mitosis [12].

Although inactivation of the basic transcriptional machinery would probably be sufficient to turn off the transcriptional activity of the cell, [3,7] multiple pathways also exist for the inactivation of arrays of specific transcription factors in mitosis [3]. Redundancy in biological processes is not uncommon, especially for critical events. On the other hand, multifaceted effects of biological processes are not uncommon either. The implications of mitotic division extend beyond the numeric increase of cellular populations. Interestingly, many of the inhibitory pathways of transcription factors during mitosis are associated with reduced DNA binding affinity which results in exclusion of these factors from condensed DNA. This massive reshuffling and redistribution of proteins has been proposed to be a window for the reestablishment of gene regulation and expression programs [45]. Further investigation of the global inactivation of the $C_2H_2$ ZFPs could also provide significant insights into the understanding of cellular differentiation and developmental transitions.

Zinc finger modules have also been shown to mediate protein-protein interactions [46]. Although this aspect of the zinc finger function is significantly less studied than DNA binding activity, it is well established for many proteins [46-48]. In addition, these types of interactions have been shown to be regulated by phosphorylation in several contexts [47, 48]. The role of ZFP linker peptides in protein-protein interactions is not clear. An interesting possibility to consider is that linker phosphorylation could also affect protein-protein interactions and mediate mitosis-specific protein complex formation or impact the equal distribution (or segregation) of ZFPs into the two new daughter cells. For example, mitotic ZFP Sp1 was shown to biochemically associate with F-actin [49]. In addition, Sp1 foci were shown to colocalize with microfilaments during mitosis [49].

The high abundance and mitotic exclusivity of the HpTGEKP phospho-epitope make it an excellent candidate for use as a mitotic and proliferation marker. Proliferation biomarkers are of indispensable value in cell cycle research. More importantly, many of these markers have been translated into valuable cancer prognostic and diagnostic tools, [50] particularly those used to assess the mitotic index of a cellular mixture [51-54]. In this study we have shown the capacity of the α-HpTGEKP antibody for the calculation of the mitotic index, whether with the microscope or in a more automated approach, when coupled with flow cytometry. Although the mitotic occurrence and exclusivity of this event was observed in all of the cell types that we tested, differences were observed in the intensity and the banding patterns of the HpTGEKP containing proteins among different cell types. An intriguing possibility is that this could be due to tissue specific expression of some ZFPs, tissue specific differences in the regulation of this phosphorylation pathway, or both. Also, these differences are observed in cells derived from different cancers types.

Finally, the identification of the kinase(s) and the signaling pathways governing this global mitotic event is importance. Elucidation of these pathways will have significant implications on our understanding of cellular division and differentiation, possibly presenting novel therapeutic targets for proliferative diseases, such as cancer. The identification of this kinase has been challenging since the conserved linker elements do not conform to known phosphorylation consensus sites. Previous attempts to identify the linker kinase were not successful [12]. Current work in our laboratory is focused on identifying the kinase(s) responsible for the global phosphorylation of $C_2H_2$ ZFPs during mitosis.

Experimental Details

This section explains the sample preparations, experimental protocols, and measurement techniques used in the above described examples. Nothing in this section should be considered as limiting the scope of the invention in any way.

Cell Culture and Synchronization.

HeLa, HeLa-Flag-YY1, and U2OS cells were grown at 37° C. in 5% $CO_2$ in DMEM (Cellgro, Cat#10-013-CV) with 2 mM L-glutamine. For BJ cells, the growth medium was supplemented with 1% nonessential amino acids (Sigma, Cat# M7145). HCT116 cells were grown in McCoy's 5A medium (Cellgro, Cat#10-050-CV). All growth media were supplemented with 10% fetal bovine serum (FBS; Sigma, Cat# F0926) and 1% penicillin-streptomycin (Cellgro, Cat#30-002-CI). HeLa-Flag-YY1 is a stable cell line overexpressing Flag-YY1, constructed as previously described.[27] Blocking cells at pro-metaphase of mitosis was performed by adding nocodazole (Sigma, Cat# M1404) (50 ng/ml) for 18 hours. To block cells in S-phase, thymidine (Sigma, Cat# T1895) was added to a final concentration of 2 mM for 18 hours. For double-thymidine synchronization at early S-phase, cells were blocked for 18 hours, released for 9 hours, and blocked again for 17 hours.

Plasmids and Transfections.

pCS2(+)-Flag-YY1 wild type (WT) or (T348A) mutant were constructed as previously described [27]. For transient overexpression, cells were transected with Lipofectamine 2000 transfection reagent (Invitrogen, Cat#11668-019), according to the manufacturer instructions.

Antibodies.

α-YY1 (Cat# sc-7341), α-cyclin B1 (Cat# sc-245), α-GAPDH (Cat# sc-25778), α-Plk1 (Cat# sc-5585), α-CTCF (Cat# sc-271474), α-lamin A/C (Cat# sc-7292), α-pH3S10 (Cat# sc-8656-R), and α-GFP (Cat# sc-9996) antibodies were purchased from Santa Cruz Biotechnology. α-Flag (Resin M2) antibody was purchased from Sigma (Cat# A2220).

α-HpTGEKP was raised as a rabbit polyclonal antibody against the phospho-antigen Ac-C(Ahx)HpTGEKP-amide and was prepared according to the inventor's instructions by New England Peptide company. A deposit of purified α-HpTGEKP is stored in the inventors' laboratory.

WCE, immunoprecipitation (IP), and Western blotting were performed as previously described [27]. Briefly, for WCE preparation, cells were washed with ice-cold PBS, and lysed in freshly prepared lysis buffer (50 mM Tris pH 7.4, 150 mM NaCl, 0.5% Triton-X 100, 1 mM EDTA, 2.5 mM EGTA, 10 mM NaF, and 5 mM glycerophosphate), on ice. For IP, cell lysates were pre-cleared with protein A/G agarose beads (Santa Cruz, Cat# sc-2003) for 2 hours at 4° C. For CTCF IP, cell lysates were incubated with α-CTCF for 3 hours at 4° C. followed by addition of protein A/G beads for an additional hour. For α-Flag IP, resin-coupled antibody (M2) was added for 4 hours.

For phosphatase treatment, WCEs or IPs were incubated at 30° C. for 1 hour with or without Lambda phosphatase (New England Biolabs, Cat# P0753), in the presence of 2 mM $MnCl_2$.

For Western blotting of WCE and IPs, proteins were separated on SDS-PAGE gels and transferred to a nitrocellulose membrane. After transfer, membranes were blocked in TBSTM (Tris-buffered saline, 0.5% Tween20, 5% Milk) for 30 minutes. Probing with the indicated primary antibodies was for 2 hours at room temperature (RT), or overnight at 4° C. Horseradish peroxidase (HRP)-conjugated anti-mouse and anti-rabbit secondary antibodies (GE Healthcare, Cat# NA934V) were added for 1 hour at RT. Visualization of bands was by exposure to X-ray films after incubating the membrane with SuperSignal West Pico Chemiluminescent Substrate (Pierce, Cat#34078).

For the dot-blot experiment, synthetic peptides HTGEKP (SEQ ID NO: 2) (non-phosphorylated) and HpTGEKP were custom synthesized for to inventors by New England Peptide. Indicated amount of peptides were spotted on a nitrocellulose membrane and allowed to dry for 1 hour. Then, the membrane was wetted in blocking buffer and probed as indicated above.

For the antibody pre-blocking experiment, α-HpTGEKP was incubated overnight at 4° C. with 1 µg/ml of HTGEKP (SEQ ID NO: 2) or HpTGEKP peptides in blocking solution, before addition to the WCE blot.

Indirect Immunofluorescence.

Cells seeded on coverslips were grown and synchronized as mentioned above and indicated in the figures. For immunostaining, cells were fixed with 3.7% formaldehyde for 10 minutes at RT, followed by permeabilization for 10 minutes with 0.2% Triton-X 100. Cells were blocked in TBST (with 3% IgG-free BSA) for an hour, then incubated with the indicated primary antibodies for 1 hour at RT. Anti-mouse and anti-rabbit secondary antibodies, conjugated to Alexa-Fluor 546 (Cat# A10040) and 647 dyes (Cat#31571), were purchased from Molecular Probes. DNA was stained with DAPI (2 µg/ml). For phosphatase treatment, fixed cells on coverslips were incubated at 30° C. for 1 hour with or without Lambda phosphatase, in the presence of 2 mM $MnCl_2$. Images were captured using a confocal fluorescent microscope (Leica micro-systems).

Flow Cytometry.

For flow cytometry analysis, cells were collected by trypsinization. For cell cycle analysis based on DNA content, cells were fixed with 70% ethanol, washed and resuspended in propidium iodide (PI) solution (50 µg/ml PI, 200 µg/ml RNase A, 0.1% Triton-X 100 in PBS) and incubated for 30 min at 30° C. For counting and enrichment of mitotic cells based on HpTGEKP staining, indirect immunostaining was performed as detailed above. For this procedure, cells were immunostained in suspension using α-HpTGEKP or α-pH3S10 as primary antibodies, then with Alexa-Fluor 488 conjugated anti-rabbit secondary antibody (Molecular Probes, Cat# A-11017). Cells were analyzed on a fluorescence-activated cell sorter (FACS; FACS Canto; Becton Dickinson), and images were generated using BD FACS Diva software. For counting and enrichment of mitotic cells gating was adjusted based on the positive HpTGEKP signal (as shown in FIGS. 11-14). Enrichment of mitotic cells was performed on a FACSAria instrument.

The present invention has been described hereinabove with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical figures expressed herein are intended to be approximate and not an exact or critical figure unless expressly stated to the contrary.

Further, any publications, patent applications, patents, and other references mentioned herein are incorporated by reference in their entirety as if they were part of this specification. However, in case of conflict, the present specification, including any definitions, will control. In addition, as noted above, materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

Any element in a claim that does not explicitly state "means for" performing a specified function, or "step for"

performing a specified function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

TABLE 1

| Protein name | AA | TGEKP Seq. position | Accession No. |
|---|---|---|---|
| Aiolos | 509 | 169-173 [55] | NP_036613 |
| BCL-11A | 835 | 400-405 | NP_075044 |
| CTCF | 727 | 518-522 | NP_006556 |
| EGR1 | 543 | 391-395 | NP_001955 |
| FLT3-interacting zinc finger 1 | 496 | 102-106; 437-441 | NP_116225 |
| GFI1 | 422 | 363-367 | NP_001120688 |
| GLI1 | 1106 | 296-300; 326-330 | NP_005260 |
| HKR1 | 659 | 380-384; 436-440; 492-496 | NP_861451 |
| IKZF5 | 419 | 105-109; 133-137 | NP_071911 |
| KLF1 | 362 | 304-308 | NP_006554 |
| MTF1 | 753 | 254-258 | NP_005946 |
| Myoneurin | 610 | 353-357; 438-442; 466-470 | NP_001172047 |
| Myeloid zinc finger 1 | 734 | 592-596; 620-624 | NP_003413 |
| RBAK | 714 | 284-288; 424-428; 590-594 | NP_001191385 |
| SALL1 | 1324 | 1157-1161 | NP_002959 |
| SCRT2 | 307 | 235-239 | NP_149120 |
| SNAI1 | 264 | 203-207 | NP_005976 |
| Transcription Factor IIIA | 365 | 95-99 | NP_002088 |
| TIP20 | 382 | 117-121 [55,56]; 145-149 [56] | NP_001002836 |
| WT1 | 497 | 399-403; 457-461 | NP_000369 |
| YY1 | 414 | 348-352 [55,57-59] | NP_003394 |
| YY2 | 372 | 306-310 [55,58,59] | NP_996806 |
| ZBTB7B | 539 | 369-373 [55] | NP_056956 |
| ZBTB16 | 673 | 569-573 [60] | NP_001018011 |
| ZNF24 | 368 | 302-306 [60]; 330-334 [60] | NP_008896 |
| ZNF28 | 718 | 350-354; 378-382; 406-410 [60]; 434-438; 490-494; 518-522; 574-578; 602-606; 630-634; 686-690 | NP_008900 |
| ZNF100 | 542 | 256-260; 284-288; 340-344 424-428 [60]; 452-456 [59]; 480-484 [59] | NP_775802 |
| ZNF107 | 783 | 155-159 [60]; 211-215; 351-355; 435-439; 463-467; 491-495 [60]; 547-551; 631-635 [60]; 659-663; 687-691; 743-747; 771-775 | NP-001013768 |
| ZNF117 | 483 | 160-164 [60]; 328-332; 356-360 | NP_056936 |
| ZNF148 | 794 | 194-198 [55]; 222-226 | NP_068799 |
| ZNF155 | 538 | 227-231; 255-259; 283-287 [55]; 311-315; 339-343; 367-371 | NP_003436 |
| ZNF187 | 478 | 333-337; 417-421 [55] | NP_001104509 |
| ZNF195 | 629 | 433-437 [60]; 461-465; 517-521; 545-549 [60]; 573-577; 601-605 [60] | NP_001123992 |
| ZNF221 | 617 | 249-253; 277-281; 305-309 [55]; 333-337; 389-393 | NP_037491 |
| ZNF225 | 706 | 227-231 [55]; 283-287 55]; 367-371; 619-623 | NP_037494 |
| ZNF226 | 803 | 386-390[55]; 414-418; 442-446; 498-502; 526-530; 582-586; 610-614; 694-698; 722-726; 750-754 | NP_001027545 |
| ZNF234 | 700 | 283-287[55]; 311-315; 339-343; 367-371; 395-399; 423-427; 479-483; 507-511; 563-567; 591-595; 619-623; 647-651 | NP_006621 |
| ZNF230 | 474 | 219-223[55]; 247-251; 275-279 | NP_006291 |
| ZNF235 | 738 | 338-342; 366-370; 394-398; 422-426; 478-482; 506-510; 534-538; 562-566; 590-594; 618-622; 646-650 [55]; 674-678 | NP_004225 |
| ZNF254 | 659 | 345-349; 429-433; 485-489; 513-517; 569-573[6] | NP_975011 |

TABLE 1-continued

| Protein name | AA | TGEKP Seq. position | Accession No. |
|---|---|---|---|
| ZNF267 | 743 | 403-407; 431-435 [60]; 487-491; 543-547; 571-575; 599-603 | NP_003405 |
| ZNF283 | 679 | 258-262; 286-290; 342-346; 398-402; 426-430; 454-458; 510-514; 538-542; 566-570[55] | NP_862828 |
| ZNF407 | 2248 | 1651-1655 [55]; 1709-1713; 1737-1741 | NP_060227 |
| ZNF479 | 524 | 264-268; 320-324; 376-380; 488-492 [60]; 516-520 | NP_150376 |
| ZNF454 | 522 | 239-243; 267-271; 295-299 [55]; 351-355; 379-383; 407-411; 435-439; 491-495 | NP_872400 |
| ZFP1 | 407 | 207-211 [60]; 235-239; 347-351; 375-379 | NP_710155 |
| ZFP91 | 570 | 395-399 [55,60] | NP_444251 |
| ZFP95 | 839 | 369-373 [55]; 397-401; 572-576; 600-604; 796-800 | NP_659570 |
| ZFX | 805 | 571-575 [56] | NP_001171556 |
| ZFY | 801 | 567-571 [56] | NP_003402 |

REFERENCES CITED

1. Taylor J H. Nucleic acid synthesis in relation to the cell division cycle. Ann N Y Acad Sci 1960; 90:409-21.
2. Prescott D M, Bender M A. Synthesis of RNA and protein during mitosis in mammalian tissue culture cells. Exp Cell Res 1962; 26:260-8.
3. Gottesfeld J M, Forbes D J. Mitotic repression of the transcriptional machinery. Trends Biochem Sci 1997; 22:197-202.
4. Martinez-Balbas M A, Dey A, Rabindran S K, Ozato K, Wu C. Displacement of sequence-specific transcription factors from mitotic chromatin. Cell 1995; 83:29-38.
5. Guttinger S, Laurell E, Kutay U. Orchestrating nuclear envelope disassembly and reassembly during mitosis. Nat Rev Mol Cell Biol 2009; 10:178-91.
6. Bellier S, Dubois M F, Nishida E, Almouzni G, Bensaude O. Phosphorylation of the RNA polymerase II largest subunit during Xenopus laevis oocyte maturation. Mol Cell Biol 1997; 17:1434-40.
7. Gebara M M, Sayre M H, Corden J L. Phosphorylation of the carboxy-terminal repeat domain in RNA polymerase II by cyclin-dependent kinases is sufficient to inhibit transcription. J Cell Biochem 1997; 64:390-402.
8. Long J J, Leresche A, Kriwacki R W, Gottesfeld J M. Repression of TFIIH transcriptional activity and TFIIH-associated cdk7 kinase activity at mitosis. Mol Cell Biol 1998; 18:1467-76.
9. Luscher B, Eisenman R N. Mitosis-specific phosphorylation of the nuclear oncoproteins Myc and Myb. J Cell Biol 1992; 118:775-84.
10. Segil N, Roberts S B, Heintz N. Mitotic phosphorylation of the Oct-1 homeodomain and regulation of Oct-1 DNA binding activity. Science 1991; 254:1814-6.
11. Caelles C, Hennemann H, Karin M. M-phase-specific phosphorylation of the POU transcription factor GHF-1 by a cell cycle-regulated protein kinase inhibits DNA binding. Mol Cell Biol 1995; 15:6694-701.
12. Dovat S, Ronni T, Russell D, Ferrini R, Cobb B S, Smale S T. A common mechanism for mitotic inactivation of C2H2 zinc finger DNA-binding domains. Genes Dev 2002; 16:2985-90.

13. Tupler R, Perini G, Green M R. Expressing the human genome. Nature 2001; 409:832-3.
14. Wolfe S A, Nekludova L, Pabo C O. DNA recognition by Cys2His2 zinc finger proteins. Annu Rev Biophys Biomol Struct 2000; 29:183-212.
15. Laity J H, Lee B M, Wright P E. Zinc finger proteins: new insights into structural and functional diversity. Curr Opin Struct Biol 2001; 11:39-46.
16. Wuttke D S, Foster M P, Case D A, Gottesfeld J M, Wright P E.
Solution structure of the first three zinc fingers of TFIIIA bound to the cognate DNA sequence: determinants of affinity and sequence specificity. J Mol Biol 1997; 273: 183-206.
17. Choo Y, Klug A. A role in DNA binding for the linker sequences of the first three zinc fingers of TFIIIA. Nucleic Acids Res 1993; 21:3341-6.
18. Thiesen H J, Bach C. DNA recognition of C2H2 zinc-finger proteins. Evidence for a zinc-finger-specific DNA recognition code. Ann N Y Acad Sci 1993; 684:246-9.
19. Cui X, Ji D, Fisher D A, Wu Y, Briner D M, Weinstein E J. Targeted integration in rat and mouse embryos with zinc-finger nucleases. Nat Biotechnol 2011; 29:64-7.
20. Jamieson A C, Miller J C, Pabo C O. Drug discovery with engineered zinc-finger proteins. Nat Rev Drug Discov 2003; 2:361-8.
21. Klug A. The discovery of zinc fingers and their applications in gene regulation and genome manipulation. Annu Rev Biochem 2010; 79:213-31.
22. Santiago Y, Chan E, Liu P Q, Orlando S, Zhang L, Urnov F D, et al. Targeted gene knockout in mammalian cells by using engineered zinc-finger nucleases. Proc Natl Acad Sci USA 2008; 105:5809-14.
23. Thukral S K, Morrison M L, Young E T. Alanine scanning site-directed mutagenesis of the zinc fingers of transcription factor ADR1: residues that contact DNA and that transactivate. Proc Natl Acad Sci USA 1991; 88:9188-92.
24. Clemens K R, Zhang P, Liao X, McBryant S J, Wright P E,
Gottesfeld J M. Relative contributions of the zinc fingers of transcription factor IIIA to the energetics of DNA binding. J Mol Biol 1994; 244:23-35.
25. Laity J H, Dyson H J, Wright P E. DNA-induced alpha-helix capping in conserved linker sequences is a determinant of binding affinity in Cys(2)-His(2) zinc fingers. J Mol Biol 2000; 295:719-27.
26. Jantz D, Berg J M. Reduction in DNA-binding affinity of Cys2His2 zinc finger proteins by linker phosphorylation. Proc Natl Acad Sci USA 2004; 101:7589-93.
27. Rizkallah R, Hurt M M. Regulation of the transcription factor YY1 in mitosis through phosphorylation of its DNA-binding domain. Mol Biol Cell 2009; 20:4766-76.
28. Dephoure N, Zhou C, Villen J, Beausoleil S A, Bakalarski C E,
Elledge S J, et al. A quantitative atlas of mitotic phosphorylation. Proc Natl Acad Sci USA 2008; 105:10762-7.
29. Chen R Q, Yang Q K, Lu B W, Yi W, Cantin G, Chen Y L, et al.
CDC25B mediates rapamycin-induced oncogenic responses in cancer cells. Cancer Res 2009; 69:2663-8.
30. Mayya V, Lundgren D H, Hwang S I, Rezaul K, Wu L, Eng J K, et al. Quantitative phosphoproteomic analysis of T cell receptor signaling reveals system-wide modulation of protein-protein interactions. Sci Signal 2009; 2:ra46.
31. Olsen J V, Vermeulen M, Santamaria A, Kumar C, Miller M L, Jensen L J, et al. Quantitative phosphoproteomics reveals widespread full phosphorylation site occupancy during mitosis. Sci Signal 2010; 3:ra3.
32. Moritz A, Li Y, Guo A, Villen J, Wang Y, MacNeill J, et al. Akt-RSK-S6 kinase signaling networks activated by oncogenic receptor tyrosine kinases. Sci Signal 2010; 3:ra64.
33. Sullivan M, Morgan D O. Finishing mitosis, one step at a time. Nat Rev Mol Cell Biol 2007; 8:894-903.
34. Shi Y, Lee J S, Galvin K M. Everything you have ever wanted to know about Yin Yang 1. Biochim Biophys Acta 1997;
1332:F49-66.
35. Gordon S, Akopyan G, Garban H, Bonavida B. Transcription factor YY1: structure, function, and therapeutic implications in cancer biology. Oncogene 2006; 25:1125-42.
36. Castellano G, Torrisi E, Ligresti G, Malaponte G, Militello L, Russo A E, et al. The involvement of the transcription factor Yin Yang 1 in cancer development and progression.
Cell Cycle 2009; 8:1367-72.
37. Zaravinos A, Spandidos D A. Yin yang 1 expression in human tumors. Cell Cycle 2010; 9:512-22.
38. Bushmeyer S, Park K, Atchison M L. Characterization of functional domains within the multifunctional transcription factor, YY1. J Biol Chem 1995; 270:30213-20.
39. Austen M, Luscher B, Luscher-Firzlaff J M. Characterization of the transcriptional regulator YY1. The bipartite transactivation domain is independent of interaction with the TATA box-binding protein, transcription factor IIB,
TAFII55, or cAMP-responsive element-binding protein (CPB)-binding protein. J Biol Chem 1997; 272:1709-17.
40. Phillips J E, Corces V G. CTCF: master weaver of the genome.
Cell 2009; 137:1194-211.
41. Martin D, Pantoja C, Minan A F, Valdes-Quezada C, Molto E,
Matesanz F, et al. Genome-wide CTCF distribution in vertebrates defines equivalent sites that aid the identification of disease-associated genes. Nat Struct Mol Biol 2011.
42. Hans F, Dimitrov S. Histone H3 phosphorylation and cell division. Oncogene 2001; 20:3021-7.
43. Nowak S J, Corces V G. Phosphorylation of histone H3: a balancing act between chromosome condensation and transcriptional activation. Trends Genet 2004; 20:214-20.
44. Johansen K M, Johansen J. Regulation of chromatin structure by histone H3S10 phosphorylation. Chromosome Res 2006; 14:393-404.
45. Egli D, Birkhoff G, Eggan K. Mediators of reprogramming: transcription factors and transitions through mitosis. Nat Rev Mol Cell Biol 2008; 9:505-16.
46. Brayer K J, Segal D J. Keep your fingers off my DNA: protein-protein interactions mediated by C2H2 zinc finger domains.
Cell Biochem Biophys 2008; 50:111-31.
47. Jones D R, Prasad A A, Chan P K, Duncker B P. The Dbf4 motif C zinc finger promotes DNA replication and mediates resistance to genotoxic stress. Cell Cycle 2010; 9:2018-26.
48. Dudekula S, Lee M H, Hsu L J, Chen S J, Chang N S. Zfra is a small wizard in the mitochondrial apoptosis. Aging (Albany N.Y.) 2010; 2:1023-9.
49. He S, Davie J R. Sp1 and Sp3 foci distribution throughout mitosis. J Cell Sci 2006; 119:1063-70.
50. Whitfield M L, George L K, Grant G D, Perou C M. Common markers of proliferation. Nat Rev Cancer 2006; 6:99-106.

51. Baak J P, Gudlaugsson E, Skaland I, Guo L H, Klos J, Lende T H, et al. Proliferation is the strongest prognosticator in node-negative breast cancer: significance, error sources, alternatives and comparison with molecular prognostic markers. Breast Cancer Res Treat 2009; 115:241-54.

52. Colman H, Giannini C, Huang L, Gonzalez J, Hess K, Bruner J, et al. Assessment and prognostic significance of mitotic index using the mitosis marker phospho-histone H3 in low and intermediate-grade infiltrating astrocytomas. Am J Surg Pathol 2006; 30:657-64.

53. Kim Y J, Ketter R, Steudel W I, Feiden W. Prognostic significance of the mitotic index using the mitosis marker anti-phosphohistone H3 in meningiomas. Am J Clin Pathol 2007; 128:118-25.

54. van Diest P J, van der Wall E, Baak J P. Prognostic value of proliferation in invasive breast cancer: a review. J Clin Pathol 2004; 57:675-81.

55. Dephoure N, Zhou C, Villen J, Beausoleil S A, Bakalarski C E, Elledge S J, et al. A quantitative atlas of mitotic phosphorylation. Proc Natl Acad Sci USA 2008; 105:10762-7.

56. Chen R Q, Yang Q K, Lu B W, Yi W, Cantin G, Chen Y L, et al. CDC25B mediates rapamycin-induced oncogenic responses in cancer cells. Cancer Res 2009; 69:2663-8.

57. Rizkallah R, Hurt M M. Regulation of the transcription factor YY1 in mitosis through phosphorylation of its DNA-binding domain. Mol Biol Cell 2009; 20:4766-76.

58. Mayya V, Lundgren D H, Hwang S I, Rezaul K, Wu L, Eng J K, et al. Quantitative phosphoproteomic analysis of T cell receptor signaling reveals system-wide modulation of protein-protein interactions. Sci Signal 2009; 2:ra46.

59. Olsen J V, Vermeulen M, Santamaria A, Kumar C, Miller M L, Jensen L J, et al. Quantitative phosphoproteomics reveals widespread full phosphorylation site occupancy during mitosis. Sci Signal 2010; 3:ra3.

60. Moritz A, Li Y, Guo A, Villen J, Wang Y, MacNeill J, et al. Akt-RSK-S6 kinase signaling networks activated by oncogenic receptor tyrosine kinases. Sci Signal 2010; 3:ra64.

That which is claimed is:

1. A method of immunostaining at least one mitotic cell, the method comprising contacting the at least one mitotic cell with an antibody having specific binding affinity for a cellular marker indicative of the mitotic state, the marker comprising SEQ ID NO: 2 phosphorylated at threonine, wherein the antibody has no specific binding affinity for SEQ ID NO: 2 when SEQ ID NO: 2 is not phosphorylated at threonine.

2. The method of claim 1, wherein the antibody is generated with a peptide consisting of SEQ ID NO: 2 phosphorylated at threonine.

3. The method of claim 1, wherein the antibody is polyclonal.

4. The method of claim 1, wherein the cells are mammalian.

5. The method of claim 1, further comprising staining the at least one cell with a secondary antibody.

6. The method of claim 5, wherein the secondary antibody comprises a fluorophore.

7. A reagent kit comprising an antibody having specific binding affinity for an amino acid sequence comprising SEQ ID NO: 2 phosphorylated at threonine, the antibody having no specific binding affinity for SEQ ID NO: 2 when SEQ ID NO: 2 is not phosphorylated at threonine.

8. The kit of claim 7, wherein the antibody is polyclonal.

9. The kit of claim 7, wherein the antibody is generated with a peptide consisting of SEQ ID NO: 2 phosphorylated at threonine.

10. An isolated antibody that has a specific binding affinity for a polypeptide comprising SEQ ID NO: 2 phosphorylated at threonine and has no specific binding affinity for SEQ ID NO: 2 when SEQ ID NO: 2 is not phosphorylated at threonine.

11. The isolated antibody of claim 10, wherein the antibody is polyclonal.

12. The isolated antibody of claim 10, wherein the antibody is generated with a peptide consisting of SEQ ID NO: 2 phosphorylated at threonine.

* * * * *